United States Patent [19]

Murao et al.

[11] Patent Number: 4,567,300

[45] Date of Patent: Jan. 28, 1986

[54] PROCESS FOR PRODUCING N-SUBSTITUTED FORMAMIDES

[75] Inventors: Yoshikazu Murao, Machida; Shigeru Sawayama; Kohichi Satoh, both of Yokohama, all of Japan

[73] Assignee: Mitsubishi Chemical Industries Limited, Tokyo, Japan

[21] Appl. No.: 690,252

[22] Filed: Jan. 10, 1985

[30] Foreign Application Priority Data

Jan. 14, 1984 [JP] Japan .................................. 59-5232
Mar. 13, 1984 [JP] Japan ................................ 59-47967

[51] Int. Cl.$^4$ .......................................... C07C 103/127
[52] U.S. Cl. ................................................. 564/215
[58] Field of Search ......................................... 564/215

[56] References Cited

U.S. PATENT DOCUMENTS

| | | | |
|---|---|---|---|
| 2,603,661 | 7/1952 | Bruce et al. | 564/215 X |
| 3,424,791 | 1/1969 | Kurtz et al. | 260/558 |
| 3,526,620 | 9/1970 | Bestian et al. | 564/215 X |
| 3,531,471 | 9/1970 | Hartwimmer et al. | 564/215 X |
| 3,822,306 | 7/1974 | Becke et al. | 260/465.4 |
| 3,914,304 | 10/1975 | Schnabel et al. | 564/215 |
| 3,941,666 | 3/1976 | Mitzlaff et al. | 204/79 |
| 4,036,712 | 7/1977 | Mitzlaff | 204/59 R |
| 4,322,271 | 3/1982 | Jensen et al. | 564/215 X |
| 4,334,097 | 6/1982 | Schmidt | 564/215 X |
| 4,421,602 | 12/1983 | Brunnmueller et al. | 162/168.2 |
| 4,444,667 | 4/1984 | Burkert et al. | 210/735 |

FOREIGN PATENT DOCUMENTS 1224304 9/1966 Fed. Rep. of Germany ...... 564/215 UX

Primary Examiner—Paul F. Shaver
Attorney, Agent, or Firm—Oblon, Fisher, Spivak, McClelland & Maier

[57] ABSTRACT

Disclosed herein is a process for producing N-substituted formamide represented by the formula:

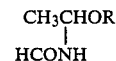

wherein R represents a hydrogen atom or a residual radical of a primary or secondary alcohol, comprising the steps of reacting formamide with acetaldehyde in the presence of a basic catalyst and if required, further reacting the thus formed product, N-(α-hydroxyethyl)-formamide, with a primary or secondary alcohol in the presence of an acid catalyst.

19 Claims, No Drawings

PROCESS FOR PRODUCING N-SUBSTITUTED FORMAMIDES

BACKGROUND OF THE INVENTION

The present invention relates to a process for producing N-substituted formamide, and more in detail, relates to a process for producing N-(α-hydroxyethyl)formamide and N-(α-alkoxyethyl)formamide, both of which are important substances as an intermediate for forming useful N-vinylformamide according to the following formulae:

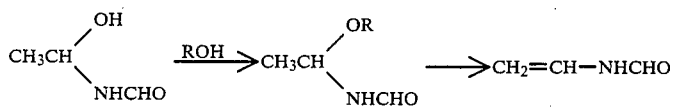

wherein R represents an alkyl group.

Hitherto, as a process for producing N-vinylformamide, there have been known a process (1) in which acetaldehydecyanhydrin obtained by reacting acetaldehyde with hydrogen cyanide, as a starting material, is reacted with formamide to form N-(α-cyanoethyl)formaldehyde and hydrogen cyanide is split off from the obtained N-(α-cyanoethyl)formamide to obtain the N-vinyl compound, and a process (2) in which N-ethylformamide is reacted with methanol by an electrode reaction to form N-(α-methoxyethyl)formamide and methanol is split off from the obtained N-(α-methoxyethyl)-formamide to obtain the N-vinyl compound, etc. However, every known process is not an industrially satisfactory method from the viewpoints of the safety of the starting material and of the operation in chemical reaction(s).

Although as a process for obtaining N-(α-methoxyethyl)formamide, a process in which α-chloroethyl methyl ether is reacted with formamide in the presence of an excess base has also been known, the process is not practical in factories because of the predominant formation of N,N-di-(α-methoxyethyl)formamide in the process.

Although the process which uses N-(α-hydroxyethyl)formamide or a reaction product thereof with an alcohol as the starting material according to the aforementioned reaction formula is an industrially advantageous process as compared with the known methods mentioned before, no report has been found on the afore-mentioned process.

Namely, the process for producing N-(α-hydroxyethyl)formamide wherein formamide which is a primary amide is reacted with acetaldehyde, and the process for producing N-(α-alkoxy-ethyl)formamide wherein N-(α-hydroxyethyl)formamide is reacted with a primary or secondary alcohol have not yet been known.

Concerning the reaction between formamide and formaldehyde, various reports have been hitherto published, and in general, N-methylol compound is obtained by the equilibrium reaction of formamide and formaldehyde. In addition, N-methoxymethylamide is formed by the reaction of N-methylolamide with methanol. Accordingly, in the reaction of an aldehyde to formamide, formaldehyde is different from acetaldehyde in its behavior in reaction, namely the reaction of formaldehyde to formamide is substantially different from the reaction of acetaldehyde to formamide.

On the other hand, a process for producing N-(α-hydroxyethyl)-N-methylformaldehyde by a reaction of a secondary amide such as N-methylformamide and acetaldehyde has been known, for instance, in Japanese Patent Publication No. 45-14283/1970. To be concrete, it is a process for producing N-(α-hydroxyethyl)-N-alkylamide by reacting a secondary amide with acetaldehyde in the presence of a strongly basic catalyst such as sodium hydroxide or potassium hydroxide or one of the various acid catalysts.

In considering the similarity of the reaction, a use of the catalyst disclosed in the above-mentioned Japanese Patent Publication in the reaction between formamide and acetaldehyde has been examined by the present inventors and as a result, in the case of using a strongly basic catalyst, the yield of N-(α-hydroxyethyl)formamide did not attain the expected level of practical use, and in the case of using an acid catalyst, N,N'-ethylidene-bisformamide was formed without producing the object compound.

As has been described, the reaction conditions for industrial production of N-(α-hydroxyethyl)formamide by the reaction between formamide and acetaldehyde are to be selected by the viewpoint quite different from the reaction between formamide and formaldehyde or from the reaction between a secondary amide and acetaldehyde.

The object of the present invention is to provide an industrially profitable process for producing N-(α-hydroxyethyl)formamide and N-(α-alkoxyethyl)formamide as an intermediate raw material for N-vinylformamide, and such an object is easily attained by reacting formamide with acetaldehyde in the presence of a basic catalyst and, if required, by further reacting the reaction product with a primary or secondary alcohol in the presence of an acid catalyst.

The N-substituted formamide obtained according to the present invention is represented by the formula (I):

 (I)

wherein R represents a hydrogen atom or a residual radical of a primary or secondary alcohol, and N-vinylformamide is obtained by thermally decomposing the N-substituted formamide represented by the formula (I).

SUMMARY OF THE INVENTION

In an aspect of the present invention, there is provided a process for producing N-substituted formamide represented by the formula:

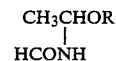

wherein R represents a hydrogen atom or a residual radical of a primary or secondary alcohol, said process comprising the steps of reacting formamide with acetaldehyde in the presence of a basic catalyst and if required, further reacting the thus obtained N-(α-hydroxyethyl)formamide with a primary or secondary alcohol in the presence of an acid catalyst.

DETAILED DESCRIPTION OF THE INVENTION:

As the catalyst for use in the reaction between formamide and acetaldehyde in the present invention, every one of the common basic compounds such as hydroxides of alkali metals, alkaline earth metals and quarternary ammonium, tertiary amines, ion-exchange resins which act strongly basic or weakly basic and weakly basic salts comprising a strong base and a weak acid may be used, however, a preferable basic catalyst is a weakly basic salt comprising a strong base and a weak acid, and particularly, a weakly basic salt comprising a strong base and a weak acid having a value of pKa in a range of from 4 to 15 at a concentration thereof of 0.01 mol/liter of an aqueous solution thereof at 25° C. is preferable.

As such a weakly basic salt, although various substances may be used, for instance, salts of a strong base such as hydroxides of lithium, sodium or potassium with a weak acid such as organic carboxylic acids, phenols, sulfurous acid, phosphorous acid, hypophosphorous acid, pyrophosphoric acid, phosphoric acid, carbonic acid, boric acid, metasilicic acid, etc. may be mentioned. As the particularly preferable weakly basic salt, potassium carbonate, sodium carbonate, potassium phosphate, sodium phosphate, potassium pyrophosphate and sodium pyrophosphate may be mentioned.

The molar ratio of formamide to acetaldehyde used as the raw materials in the reaction is selected from the range of 1:1.0 to 1:5.0, however, the preferable molar ratio depends on the manner of supplying acetaldehyde to the reaction system. Namely, in the case of supplying acetaldehyde in a gaseous state, the molar ratio is preferably in a narrower range of 1:1.0 to 1:1.5, and in the case of supplying thereof in a liquid state, the preferable molar ratio is in a range of 1:1.5 to 1:4.0.

The amount of the basic catalyst used in the reaction of formamide and acetaldehyde is suitably selected in the range of from 0.01 to 10 mol % of formamide in general, and preferably in the range of from 0.1 to 5 mol % of formamide.

Although the temperature of reaction of formamide and acetaldehyde may be selected in a broad range of −10° C. to 100° C., the preferable temperature is 0° C. to 40° C. from the viewpoint of the selectivity of product from acetaldehyde.

The process for reacting formamide with acetaldehyde may be carried out in an optional apparatus according to the various known manner, however, in the case where acetaldehyde is supplied in a gaseous state, it is possible to attain a high yield by using nearly a stoichiometrical amount of acetaldehyde and accordingly, such a way of supplying acetaldehyde is economically profitable. In a preferable manner of reaction, a catalyst and formamide are introduced into a reaction vessel provided with a stirrer and gaseous acetaldehyde is continuously fed little by little into the thus introduced liquid.

Although the reaction can be effected without using a solvent, since the reaction product, N-(α-hydroxyethyl)formamide, is a crystalline substance of a melting point of 52.5°–53.8° C., in the case where the reaction is carried out at a preferable temperature of 0° to 40° C. without using a solvent, the reaction product separates out and solidifies to be massive cakes which can not be easily taken out from the reaction vessel. Accordingly, it is preferable to carry out the reaction in the presence of a solvent. As the solvent, a solvent which is inert to the reaction and does not interfere the crystallization of N-(α-hydroxyethyl)formamide is preferable for the sake of facilitating the separation of crystals during the reaction carried out in a preferable manner which is described later. To be concrete, aliphatic hydrocarbons such as hexane and heptane, and aromatic hydrocarbons such as benzene, toluene, xylene may be mentioned. The amount of the solvent used in the reaction is suitably selected in the range of 0.2 to 2 times by weight of formamide. In addition, the solvent may be added into the reaction system just before the separation of crystals, which is described as follows.

The product of the reaction of formamide and acetaldehyde, i.e. N-(α-hydroxyethyl)formamide, is finally separated out from the reaction system as crystals, however, since the yield of the product is improved by forcibly separating out the crystals while cooling the reaction system or adding seed crystals to the reaction system during the reaction wherein separation of the crystals does not occur in a normal state, that is the conversion of formamide is 50 to 80 mol %, preferably 60 to 80 mol %. The cooling is conducted until the reaction temperature becomes in a range of −20° C. to 25° C., preferably from −5° C. to 10° C., and the addition of seed crystals is conducted by adding a small amount of crystals of N-(α-hydroxyethyl)formamide according to the known method of crystallization.

In the process wherein gaseous acetaldehyde is fed into a solution of formamide and the catalyst, the reaction proceeds quickly until the conversion of formamide reaches at 60 mol %, namely, the fed acetaldehyde quickly reacts with formamide, however, thereafter the rate of reaction is reduced. On the other hand, according to the process of the present invention, after feeding the preliminarily determined residual amount of acetaldehyde into the liquid in the flask as a gas and dissolving in the liquid, the crystals of N-(α-hydroxyethyl)formaldehyde are separated out from the liquid and the reaction is continued, or the crystals are preliminarily separated out and then the residual amount of acetaldehyde may be fed to the liquid in the flask as a gas to continue the reaction.

N-(α-hydroxyethyl)formamide formed as crystals after finishing the reaction can be collected from the reaction system by a suitable means of separation such as filtration, etc.

However, the thus obtained product is hygroscopic, thermally unstable, and easily decomposed into the starting materials, formamide and acetaldehyde. Since the decomposition is accelerated in the presence of acids and bases, in the case where the crystals contain the reaction catalyst, about 10% of the product is lost by decomposition even when such crystals are carefully neutralized and filtered at a low temperature and in a nitrogen atmosphere.

On the other hand, such decomposition reaction is completely avoidable by reacting an alcohol with the crystals of N-(α-hydroxyethyl)formamide formed under cooling conditions without isolating thereof, and N-(α-alkoxyethyl)formamide can be obtained in an extremely high yield.

Although N-(a-hydroxyethyl)formamide formed in a non-crystalline state can not be isolated, after converting N-(α-hydroxyethyl)formamide into N-(α-alkoxyethyl)formamide by reacting with the alcohol in a high selectivity, the thus formed N-(α-alkoxyethyl)formamide can be collected by a known method such as distillation, etc.

As an alcohol used in the reaction with N-(α-hydroxy-ethyl)formamide according to the present invention, primary alcohols and secondary alcohols may be generally mentioned, however, from the viewpoints of the reactivity and the solubility of N-(α-hydroxyethyl)formamide, an alcohol of one to eight carbon atoms is preferable. Although polyvalent alcohol is not preferable because it produces more than two kinds of the reaction products, it does not interfere the splitting of alkoxy radical for producing N-vinylformamide.

As an example of the preferable alcohol, methanol, ethanol, n-propanol, n-butanol, isobutyl alcohol, n-pentanol, n-hexanol, n-heptanol, n-octanol, benzyl alcohol, isopropyl alcohol, s-butyl alcohol, 2-methoxyethanol, 2-ethoxyethanol, 2-propoxyethanol, 2-butoxyethanol, diethyleneglycol monomethyl ether, ethyleneglycol, propyleneglycol 1,4-butanediol, diethyleneglycol, etc. may be mentioned. Particularly preferable are primary, monovalent alcohol of one to four carbon atoms, for instance, methanol, ethanol, n-propanol, n-butanol, isobutyl alcohol, 2-methoxyethanol and 2-ethoxyethanol.

The amount of the alcohol used to react with N-(α-hydroxyethyl)formamide can be optionally determined, however, since N-(α-hydroxyethyl)formamide is thermally unstable and it is difficult to recover N-(α-hydroxyethyl)formamide after the reaction with the alcohol is over, it is preferable to use the same or larger molar amount of alcohol, and in general, alcohol 1.0 to 30 times by mol of N-(α-hydroxyethyl)formamide is used.

Since N-(α-hydroxyethyl)formamide is a crystalline substance, it is preferable to use the alcohol for reaction as the solvent, and in such a case, the amount of alcohol used as the solvent is preferably 2.0 to 20 times by mol of N-(α-hydroxyethyl)formamide. In order to minimize the amount of alcohol, a solvent which is inert in the reaction may be suitably used.

Even in the case where a part of N-(α-hydroxyethyl)formamide is present as crystals in the reaction system, the crystals become liquid after reacting with the alcohol and accordingly, the inert solvent used herein may be a substance which dissolves N-(α-hydroxyethyl)formamide or may be a substance used simply for dispersing N-(α-hydroxyethyl)formamide. In the case of using such a solvent, the amount of the alcohol is preferably in the range from 1.0 to 5 times by mol of N-(α-hydroxyethyl)formamide.

As the catalyst used in the reaction of the alcohol and N-(α-hydroxyethyl)formamide obtained by reacting formamide with acetaldehyde, every one of the generally used acid catalysts may be used, for instance, mineral acids, organic acids, ion-exchanging resins having weak or strong acidity and solid acid catalysts. A strongly acidic substance is preferably used among them. As an example of preferable acid catalysts, sulfuric acid, hydrochloric acid, nitric acid, hydrobromic acid, sulfamic acid, methanesulfonic acid, ethanesulfonic acid, para-toluenesulfonic acid, cross-linked polystyrenesulfonic acid, etc. may be mentioned. The amount of the acid catalyst used in the reaction is 0.001 to 10mol % of N-(α-hydroxyethyl)formamide, preferably in a range of 0.1 to 5 mol %. In addition, in the case of using a catalyst of heterogeneous system such as an ion-exchanging resin, the reaction may be carried out by passing the reactants through a column packed with the catalyst.

The reaction of N-(α-hydroxyethyl)formamide and alcohol is easily carried out by adding the acid catalyst to the mixture of the two reactants or contacting the acid catalyst with the mixture of the two reactants. The temperature of the reaction is preferably in a range of $-10°$ to 60° C. from the viewpoints of the reactivity and the stability of N-(α-hydroxyethyl)formamide, and particularly in the range of 0° to 40° C. The reaction product can be isolated by a generally known means such as concentration, distillation, etc. after neutralizing or removing the catalyst.

The process according to the present invention also exhibits an especially excellent effect in the case where N-(α-hydroxyethyl)formamide obtained by reacting formamide with acetaldehyde in the presence of a basic catalyst is further reacted with an alcohol without isolating the thus obtained N-(α-hydroxyethyl)formamide. Although the reaction of the present invention does not depend on the order of addition of the alcohol and the catalyst, since N-(α-hydroxyethyl)formamide obtained by reacting formamide with acetaldehyde still contains the basic catalyst, the object product is easily obtained by (1) adding the alcohol to such N-(α-hydroxyethyl)formamide and after neutralizing thereof by the addition of an equivalent amount of an acid to the basic catalyst, adding the acid catalyst to carry out the reaction, or (2) adding the acid catalyst of larger amount than the sum of an amount necessary for neutralizing the basic catalyst and an amount necessary for the reaction. In such a case, depending on the kind of alcohol, some alcohol reacts with the unreacted acetaldehyde to easily form acetal and accordingly, it is preferable to use the alcohol in the sum of the above-mentioned amount of alcohol and the amount of the alcohol 2 times by mol to the molar amount of the unreacted acetaldehyde.

The N-substituted formamide obtained according to the present invention is a useful compound as an intermediate compound of N-vinylformamide used as the monomer of cationic polymers of polyvinylamine series which have excellent performances as the dehydrating agent for organic sludge, and the agent for improving filterability or the yield of fillers in the paper-making industry.

For instance, after thermally decomposing N-(α-alkoxyethyl)formamide in a gas phase to obtain N-vinylformamide, it is subjected to bulk polymerization, solution polymerization using an aqueous solution or an organic solution, or emulsion polymerization singly or together with a monomer used conventionally for producing water-soluble polymers for use in producing flocculants such as acrylamide, dimethylaminoethyl acrylate, dimethylaminoethyl methacrylate, acrylamidemethylpropanesulfonic acid, etc. in the presence of a polymerization initiator of azo compounds, thereby obtaining polyvinylformamide, and the thus obtained polyvinylformamide is hydrolyzed under acidic or basic conditions to obtain a cationic polymer of polyvinylamines.

The present invention will be explained more in detail while referring to the following non-limitative examples and comparative example.

EXAMPLE 1

In a 2-liter four-necked flask provided with a stirrer having impeller made of a fluorocarbon polymer, a gas inlet tube, a thermometer and an ice-cooled cooling tube fitted with an exhaust tube connected to a trap containing a small amount of liquid paraffin, 270 g (6 mol) of formamide, 4.15 g (0.03 mol) of potassium carbonate and 246 g of n-hexane were introduced, and the resultant mixture was vigorously stirred while keeping the temperature thereof at 25° C.

Separately, after introducing about 350 g of acetaldehyde into a 500-ml glass pressure bottle provided with a needle valve, the needle valve was connected to the above-mentioned gas inlet tube of the flask and while keeping the temperature of the glass pressure bottle at 40° to 45° C. acetaldehyde was fed into the flask while observing the trap containing liquid paraffin, at a maximum speed such that acetaldehyde did not leak from the trap. It took 195 min. to feed 299 g (6.79 mol) of acetaldehyde. After leaving the reaction mixture for one hour at 25° C., a part of the thus formed colourless and transparent viscous liquid in the flask was analyzed by liquid chromatography, and it was found that (1) the conversion of formamide was 83.7 mol %, (2) the selectivity of formamide to N-($\alpha$-hydroxyethyl)formamide was 100 mol %, (3) the conversion of acetaldehyde was 77 mol % and (4) the selectivity of acetaldehyde to N-($\alpha$-hydroxyethyl)-formamide was 96 mol %.

Thereafter, the flask was cooled to 10° C. and kept at the temperature for 30 min., thereafter the reaction product crystallized and the temperature of the reaction mixture of the flask was raised to 42° C. After cooling the flask again to 5° C. and keeping the reaction mixture at the temperature for one hour, a part of the reaction product was analyzed as mentioned above. It was found that the conversion of formamide was 99.2 mol % and the selectivity of formaldehyde to N-($\alpha$-hydroxyethyl)-formamide was 100 mol %.

After adding 500 ml of cooled acetone to the reaction mixture of the flask, a solution of 3.03 g of concentrated sulfuric acid in 30 g of isopropyl alcohol was further added to the flask at 5° C. and potassium carbonate in the reaction mixture was neutralized.

The product in the flask was subjected to filtration under cooling in a flow of gaseous nitrogen, and the thus collected material was washed with ice-cooled acetone and dried under a reduced pressure at room temperature to obtain 481 g of white crystals (yield: 90%). By recrystallizing the crystals by acetone, crystals of the melting point of 52.5°–53.8° C. were obtained. As are shown below, the elementary analysis data of the crystalline product substantially coincided with the calculated data of N-($\alpha$-hydroxyethyl)formamide. The structure of the product was confirmed by I.R. spectrum and N.M.R. spectrum thereof.

|  | C(%) | H(%) | N(%) |
|---|---|---|---|
| Found: | 40.18 | 7.88 | 15.59 |
| Calcd. as $C_3H_7NO_2$: | 40.44 | 7.92 | 15.72 |

EXAMPLES 2 to 11, and COMPARATIVE EXAMPLE 1

In a 200-ml four-necked flask provided with a stirrer having impeller made of a fluorocarbon polymer, a gas inlet tube, a thermometer, and an ice-cooled cooling tube fitted with an exhaust tube connected to a trap containing a small amount of liquid paraffin, 45 g of formamide and a basic catalyst (shown in Table 1) in an amount of 0.5 mol % to formamide were introduced, and the resultant mixture of the flask was vigorously stirred while heating the mixture by immersing the flask in a water bath at a predetermined temperature shown in Table 1.

Separately, after introducing a predetermined amount shown in Table 1 of acetaldehyde into a 100-ml glass pressure bottle provided with a needle valve, the needle valve was connected to the trap of the flask, and while heating the pressure bottle at 40° to 45° C., acetaldehyde was fed into the liquid material of the flask in a gaseous state at a maximum rate such that acetaldehyde did not leak from the trap in a gaseous state while observing the trap.

After having fed a predetermined amount of acetaldehyde shown in Table 1, a part of the reaction mixture was collected and analyzed by liquid chromatography to examine the composition of the product.

On cooling the flask to 5° C. while stirring the reaction mixture thereof for 30 min, the liquid reaction mixture solidified to be white crystals which were analyzed by liquid chromatography to examine the composition of the crystal.

From the composition of the product found after finishing the supply of acetaldehyde and before solidification of the product, the conversion of formamide, the selectivity of formamide to the object product, the conversion of acetaldehyde and the selectivity of acetaldehyde to the object product were calculated and shown in Table 1 together with the conversion of formamide and the selectivity of formaldehyde to the object product obtained by calculation of the composition of the crystal. It was found that a part of acetaldehyde was lost during crystallization by evaporation due to the heat generated by crystallization.

In Comparative Example 1, any catalyst was not used.

TABLE 1

| Example or Comparative Example | Catalyst | Temperature (°C.) | Acetaldehyde Amount[1] (times mol) | Time[2] (min) | Before crystallization Formamide Conversion | Select. | Acetaldehyde Conversion | Select. | After crystallization Formamide Conversion | Select. | Remarks |
|---|---|---|---|---|---|---|---|---|---|---|---|
| Example | | | | | | | | | | | |
| 2 | $K_2CO_3$ | 25 | 1.16 | 170 | 83.9 | 100 | 71.2 | 99 | 98.9 | 100 | |
| 3 | $K_2CO_3$ | 10 | 1.20 | 220 | 78.8 | 99 | 66.7 | 99 | 99.3 | 100 | |
| 4 | $Na_2CO_3$ | 25 | 1.20 | 155 | 86.4 | 99 | 76.2 | 95 | 97.5 | 99 | 3 |
| 5 | $Na_2CO_3$ | 30 | 1.21 | 150 | 76.9 | 100 | 69.1 | 92 | 97.0 | 100 | 3 |
| 6 | $Na_2CO_3$ | 40 | 1.22 | 150 | 69.7 | 100 | 79.4 | 72 | 89.0 | 100 | 3 |
| 7 | $Na_2CO_3$ | 50 | 1.74 | 225 | 57.9 | 98 | 47.2 | 69 | 77.1 | 98 | 3 |
| 8 | $K_4P_2O_7$ | 25 | 1.2 | 140 | 79.5 | 100 | 74.4 | 89 | 96.0 | 98 | 3 |

Unit of Conversion and Selectivity: mol %

TABLE 1-continued

| | | | | | Unit of Conversion and Selectivity: mol % | | | | | | |
|---|---|---|---|---|---|---|---|---|---|---|---|
| Example or Comparative Example | Catalyst | Temperature (°C.) | Acetaldehyde | | Before crystallization | | | | After crystallization | | Remarks |
| | | | Amount[1] (times mol) | Time[2] (min) | Formamide | | Acetaldehyde | | Formamide | | |
| | | | | | Conversion | Select. | Conversion | Select. | Conversion | Select. | |
| 9 | Na$_3$PO$_4$ | 25 | 1.18 | 150 | 73.7 | 100 | 77.0 | 81 | 90.4 | 100 | 3 |
| 10 | KOH | 25 | 1.16 | 120 | 45.9 | 100 | 43.5 | 91 | Not crystallized | | 3 |
| 11 | (CH$_3$)$_3$N | 25 | 1.25 | 150 | 34.1 | 100 | 51.6 | 53 | Not crystallized | | 3 |
| Comparative Example 1 | Not used | 25 | 1.14 | 120 | 0.4 | 0 | 17.1 | 0 | Not crystallized | | |

Notes:
[1] Amount fed to formamide
[2] Time for feeding
[3] After cooling, seed crystals were added in an amount of 50 mg.

EXAMPLE 12

In a 300-ml four-necked flask provided with a stirrer having impeller made of a fluorocarbon polymer, a thermometer, an ice-cooled cooling tube and a dropping funnel, 45 g of formamide and 2.65 g of potassium carbonate (2.5 mol % to formaldehyde) were introduced, and while stirring and heating the resultant mixture of the flask at 30° C., 132 g of acetaldehyde were added from the dropping funnel to the flask at an interval of 5 min with each twelveth amount thereof. The temperature of the reaction mixture of the flask elevated to a maximum of 43° C. After finishing the dropping in one hour, the reaction mixture of the flask was kept at 30° C. for one hour. On analyzing a part of the reaction product (a transparent viscous liquid) by liquid chromatography, it was found that (1) conversion of formamide was 87.6 %, (2) selectivity of formamide to N-(α-hydroxyethyl)formamide was 100%, (3) conversion of acetaldehyde was 53.3% and (4) selectivity of acetaldehyde to N-(α-hydroxyethyl)formamide was 55%.

EXAMPLES 13 to 17

In a 100-ml pear-shaped flask provided with an ice-cooled cooling tube, 17.8 g (0.2 mol) of N-(α-hydroxyethyl)formamide obtained in Example 1 and 0.6 mol of an alcohol shown in Table 2 were introduced, and while heating the flask at 20° C., the reaction mixture was stirred with a magnetic stirrer. Then solution of 98 mg of sulfuric acid in 2 g of the alcohol shown in Table 2 was added to the flask to react for 30 min. Thereafter, a part of the reaction product was collected and subjected to analysis by liquid chromatography. It was found by the analysis that conversion of formamide and selectivity of formamide to N-(α-alkoxyethyl)formamide were those shown in Table 2.

After adding 0.25 ml of an aqueous ammonia to the reaction product to neutralize thereof, the inorganic substance which was formed was removed by filtration, and the filtrate was concentrated by an evaporator. By subjecting the concentrate to distillation under a reduced pressure, the product, N-(α-alkoxyethyl)formamide was obtained. The boiling point and yield of the product was shown also in Table 2.

TABLE 2

| Example | Alcohol | Formamide after reaction | | N—(α-alkoxyethyl)-formamide | |
|---|---|---|---|---|---|
| | | Conversion (mol %) | Select. (mol %) | Boiling point (°C./mmHg) | Yield (%) |
| 13 | Methanol | 98.1 | 99 | 61–62/1.0 | 94 |
| 14 | Ethanol | 94.1 | 100 | 66.0–66.5/0.65 | 92 |
| 15 | Isopropyl alcohol | 82.6 | 99 | 56–59/0.3 | 74 |
| 16 | Butanol | 93.2 | 98 | 73–73.5/0.5 | 55[1] |
| 17 | 2-Methoxyethanol | 92.9 | 100 | 93.5/0.65 | 87 |

Note:
[1] During distillation, a part of the product was converted into N—vinylformamide thereby reducing the yield of the object product.

EXAMPLE 18

In a 100-ml pear-shaped flask provided with a cooling tube, 17.8 g (0.2 mol) of N-(α-hydroxyethyl)formamide obtained in Example 1 and 40 g (1.25 mol) of methanol were introduced, and the resultant mixture was stirred while keeping thereof at 20° C. Thereafter, 0.68 g of a dried, cross-linked polystyrene-sulfonic acid ion-exchanging resin (DIAION® PK 208H, made by MITSUBISHI Chemical Industries Ltd.) was added to the flask, and the mixture was vigorously stirred for 30 min at 20° C. After removing the resin by filtration from the reaction mixture, the filtrate was concentrated by an evaporator to obtain 20.4 g of N-(α-methoxyethyl)formamide containing 0.8% of formamide in a yield of 98%.

EXAMPLES 19 to 25

In a 500-ml four-necked flask provided with a stirrer having impeller made of a fluorocarbon polymer, a gas inlet tube, a thermometer, and an ice-cooled cooling tube fitted with an exhaust tube connected to a trap containing a small amount of liquid paraffin, 45 g of formamide (1 mol %) and 0.005 mol % a catalyst (shown in Table 3) were introduced, and the resultant mixture of the flask was vigorously stirred while keeping the mixture at 25° C.

Separately, after introducing about 65 g of acetaldehyde into a 100-ml glass pressure bottle provided with a needle valve, the needle valve was connected to the trap of the flask, and while heating the pressure bottle at 40° to 45° C., acetaldehyde was fed into the liquid material of the flask in a gaseous state at a maximum rate such that acetaldehyde did not leak from the trap in a gaseous state while observing the trap. The amount of the thus supplied acetaldehyde and the time taken for the supply are shown in Table 3.

The reaction mixture was further stirred while cooling to 5° C., and about 50 mg of crystals of N-(α-hydroxyethyl)formamide were added to the reaction mixture as seed crystals for crystallizing the reaction product. After keeping the reaction mixture for 30 min at 5° C., a solution of 0.005 mol of sulfuric acid in 96 g of methanol was added to the flask, and the mixture was stirred for 30 min. Then the reaction mixture was warmed to 20° C., and a solution of 0.005 mol of sulfuric acid in 2 g of methanol was added to the reaction mixture. After keeping the flask for 30 min at 20° C., a part of the reaction product in the flask was collected and analyzed for the composition thereof by liquid chromatography. The conversion of formamide and selectivity of formamide to N-(α-methoxyethyl)formamide are shown also in Table 3.

TABLE 3

| | Reaction of formamide and acetaldehyde | | | Reaction with methanol | | |
|---|---|---|---|---|---|---|
| Example | Time for feeding (min) | Amount of acetaldehyde used (mol) | Basic catalyst | Conversion (%) | Selectivity to Methoxy Compound (%) | Remarks |
| 19 | 120 | 1.2 | KOH | 52 | 93 | 1 |
| 20 | 130 | 1.2 | trimethylamine | 38 | 91 | 1 |
| 21 | 150 | 1.15 | $K_2CO_3$ | 99 | 96 | 2 |
| 22 | 150 | 1.15 | $K_2CO_3$ | 99 | 98 | 3 |
| 23 | 150 | 1.2 | $Na_2CO_3$ | 97 | 96 | |
| 24 | 140 | 1.2 | $K_4P_2O_7$ | 94 | 94 | |
| 25 | 150 | 1.18 | $Na_3PO_4$ | 90 | 96 | |

Notes:
[1] Did not crystallize even when seed crystals were added after the reaction with acetaldehyde was over.
[2] Crystallized by cooling when seed crystals were added after the reaction with acetaldehyde was over.
[3] Reaction was carried out in the coexistence of 45 g of n-hexane in the reaction system, thereby the thus formed crystals of N—(α-hydroxyethyl) formamide were dispersed.

What is claimed is:

1. A process for producing N-substituted formamide represented by the formula:

$$\begin{array}{c} CH_3CHOR \\ | \\ HCONH \end{array}$$

wherein R represents a hydrogen atom or the residual radical of a primary or secondary alcohol obtained by reacting N-(α-hydroxyethyl)formamide with such alcohol, as hereinafter specified, said process comprising the steps of reacting formamide with acetaldehyde in the presence of a basic catalyst and if required, further reacting the thus obtained N-(α-hydroxyethyl)formamide with a primary or secondary alcohol in the presence of an acid catalyst.

2. A process according to claim 1, wherein said reaction of formamide and acetaldehyde in the presence of the basic catalyst is carried out at a temperature of 0° C. to 40° C.

3. A process according to claim 1 or 2, wherein said acetaldehyde is fed in a gaseous state into a solution of formamide and the catalyst.

4. A process according to any one of claims 1 to 3, wherein the thus formed N-(α-hydroxyethyl)formamide is separated out from the reaction system during the reaction wherein the conversion of formamide is 50 to 80 mol % and then the reaction is continued.

5. A process for producing N-substituted formamide represented by the formula:

$$\begin{array}{c} CH_3CHOH \\ | \\ HCONH \end{array}$$

comprising the steps of reacting formamide with acetaldehyde in the presence of a basic catalyst, wherein said basic catalyst is a weakly basic salt comprising a strong base and a weak acid of a pka of 4 to 15.

6. A process according to claim 5, wherein said weakly basic salt is a salt of the strong base selected from the group consisting of hydroxides of lithium, sodium and potassium with a weak acid selected from the group consisting of organic carboxylic acids, phenols, sulfurous acid, phosphorous acid, hypophosphorous acid, pyrophosphoric acid, phosphoric acid, carbonic acid, boric acid and metasilicic acid.

7. A process according to claim 6, wherein said salt is selected from the group consisting of potassium carbonate, sodium carbonate, potassium phosphate, sodium phosphate, potassium pyrophosphate and sodium pyrophosphate.

8. A process according to claim 5, wherein a molar ratio of formamide to acetaldehyde is 1:1.0 to 5.0.

9. A process according to claim 5 wherein an amount of the basic catalyst is 0.01 to 10 mol % of formamide.

10. A process according to claim 1 wherein said primary or secondary alcohol is an alcohol having one to eight carbon atoms.

11. A process according to claim 10, wherein said primary or secondary alcohol is selected from the group consisting of methanol, ethanol, n-propanol, n-butanol, isobutyl alcohol, n-pentanol, n-hexanol, n-heptanol, n-octanol, benzyl alcohol, isopropyl alcohol, s-butyl alcohol, 2-methoxyethanol, 2-ethoxyethanol, 2-propoxyethanol, 2-butoxyethanol, diethyleneglycol monomethyl ether, ethyleneglycol, propyreneglycol, 1,4-butanediol and diethyleneglycol.

12. A process according to claim 11, wherein said primary alcohol is methanol, ethanol, n-propanol, n-butanol, isobutyl alcohol, 2-methoxyethanol and 2-ethoxyethanol.

13. A process according to claim 1, wherein said acid catalyst is selected from the group consisting of sulfuric acid, hydrochloric acid, nitric acid, hydrobromic acid, sulfamic acid, methanesulfonic acid, ethanesulfonic acid, para-toluenesulfonic acid and cross-linked polystyrenesulfonic acid.

14. A process according to claim 1, wherein an amount of the primary or secondary alcohol is 1.0 to 30 times by mol of N-(α-hydroxyethyl)formamide.

15. A process according to claim 1, wherein an amount of the acid catalyst is 0.1 to 10 mol % of N-(α-hydroxyethyl)-formamide.

16. A process including the process of claim 5 for producing N-substituted formamide represented by the formula:

$$\begin{array}{c} CH_3CHOR \\ | \\ HCONH \end{array}$$

wherein R represents the residual radical of a primary or secondary alcohol obtained by reacting N-(α-hydroxyethyl)formamide with said alcohol as hereinafter specified, said process comprising the steps of reacting the formamide with acetaldehyde in the presence of a basic catalyst as specified in claim 5 to obtain N-(α-hydroxyethyl)formamide and thereafter further reacting the thus obtained N-(α-hydroxyethyl)formamide with a primary or secondary alcohol in the presence of an acid catalyst.

17. A process according to claim 5, wherein said reaction of formamide and acetaldehyde in the presence of the weakly basic salt catalyst is carried out at a temperature of 0° C. to 40° C.

18. A process according to claim 5, wherein said acetaldehyde is fed in a gaseous state into a solution of formamide and the catalyst.

19. A process according to claim 5 wherein the thus formed N-(α-hydroxyethyl)formamide is separated out from the reaction system during the reaction wherein the conversion of formamide is 50 to 80 mol % and then the reaction is continued.

* * * * *